(12) United States Patent
Santillan et al.

(10) Patent No.: US 8,425,950 B1
(45) Date of Patent: Apr. 23, 2013

(54) LIQUID MIXTURE AND METHODS FOR USE

(76) Inventors: Victor M. Santillan, Ceres, CA (US); Monica Santillan, Ceres, CA (US)

( * ) Notice: Subject to any disclaimer, the term of this patent is extended or adjusted under 35 U.S.C. 154(b) by 0 days.

(21) Appl. No.: 13/306,943

(22) Filed: Nov. 29, 2011

(51) Int. Cl.
*A01N 65/00* (2009.01)
(52) U.S. Cl.
USPC .......................................................... 424/725
(58) Field of Classification Search .................. None
See application file for complete search history.

(56) References Cited

U.S. PATENT DOCUMENTS

| 6,503,492 | B2 | 1/2003 | McGlone et al. |
| 6,949,582 | B1 | 9/2005 | Wallace |
| 7,025,992 | B2 | 4/2006 | Whittle |
| 7,161,016 | B1 | 1/2007 | Makriyannis |
| 2005/0070596 | A1 | 3/2005 | Baker |
| 2009/0247619 | A1 | 10/2009 | Stinchcomb |
| 2010/0029778 | A1 | 2/2010 | Bailey |

*Primary Examiner* — Michael Meller

(57) ABSTRACT

A method of relieving pain includes topically applying a liquid mixture to an area of human skin. The liquid mixture includes an alcohol including concentrated ethanol, and at least one of a cannabis leaf, a cannabis stem, or a combination thereof. The method also includes absorbing the liquid mixture through the skin, providing reduced inflammation to the area, and providing increased blood flow to the area.

1 Claim, 1 Drawing Sheet

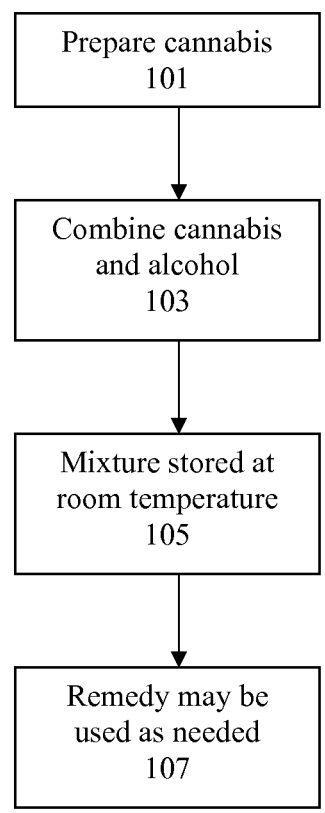

LIQUID MIXTURE AND METHODS FOR USE

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to over the counter treatments. More particularly, the invention relates to a cannabis-based topical remedy.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Many individuals experience aches, pains, swelling and discomfort caused by various different conditions such as, but not limited to, arthritis, chronic pain, injury, overuse of muscles, etc. By way of educational background, an aspect of the prior art generally useful to be aware of is that there are currently available remedies for aches, pains and swelling that may be employed by various different means including, without limitation, orally, topically, by injection, etc. It is believed that many of these current remedies may cause side effects or may be ineffective. In addition some current remedies may require a prescription from a doctor.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1 is a flowchart illustrating an exemplary method for making a cannabis-based remedy, in accordance with an embodiment of the present invention.

Unless otherwise indicated illustrations in the figures are not necessarily drawn to scale.

DETAILED DESCRIPTION OF THE PREFERRED EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

A practical embodiment of the present invention provides a topical, natural made remedy to help relieve pains and aches. Many practical embodiments comprise alcohol and the leaves and stems of the cannabis plant, which are mixed together and offered as a liquid remedy for topical use. Many practical embodiments are simple to use and work quickly by providing relief almost immediately. Applying a liquid remedy according to a practical embodiment to various parts of the body such as, but not limited to, joints, muscles, tendons, etc. typically relieves the discomfort of conditions including, without limitation, pain, aches, bruising, swelling, injury, arthritis, etc.

FIG. 1 is a flowchart illustrating an exemplary method for making a cannabis-based remedy, in accordance with an embodiment of the present invention. In one embodiment, the process begins by preparing the leaves and stems of a cannabis plant in step 101. In another embodiment, the cannabis is obtained when it is in it's mid-growing stages right before it starts to flower. In yet another embodiment, the darker green the leaves are the more effective the liquid mixture will be. In step 103 the prepared leaves and stems of the cannabis plant are combined with alcohol. Suitable alcohols include, but are not limited to, ethanol, rubbing alcohol, glycerol, ethyl alcohol, octyl alcohol, isopropyl and butyl alcohol. In one embodiment, the largest leaves of the cannabis plant are cut at the stem and removed from the rest of the plant. In another embodiment the dark green cannabis leaves are cut at the stem and removed from the rest of the cannabis plant. In one embodiment, the cannabis leaves, the cannabis stems or a combination thereof are placed in a bottle containing alcohol. In another embodiment, the cannabis leaves, the cannabis stems or a combination thereof and alcohol are mixed together in the bottle. In yet another embodiment, the bottle is turned upside down. In one embodiment, the liquid mixture is mixed to obtain a uniform distribution. In another embodiment, the liquid mixture is allowed to settle for about at least four to five days at room temperature. In yet another embodiment, the mixture is about at least 70% alcohol and about at least 30% of at least one of a cannabis leaf, a cannabis stem, or a combination thereof. It is contemplated that in some alternate embodiments, the ratio of alcohol to cannabis may be different. Furthermore, some alternate embodiments may comprise additional ingredients including, without limitation, fragrances, dyes, menthol, aloe, natural oils, water, moisturizers, etc. In the present embodiment, after the components are mixed, the mixture is stored at room temperature in step 105. It is believed that the longer the cannabis remains in the alcohol, the stronger and more potent the effect of the cannabis in the remedy will be. The remedy can then be used as needed in step 107 to relieve aches, pains, swelling, etc.

Cannabis is typically used in a cigarette form that is smoked and inhaled. This may cause side effects to other parts of the body including, without limitation, the brain. In typical use of the present embodiment, the remedy is applied topically to the problematic area of the body. The remedy may be applied by the hands of a user, or the remedy may be applied using application means such as, but not limited to, towels, napkins, sponges, swabs, cotton balls, cotton pads, etc. The remedy is for topical use and not to be taken by mouth.

It is known that cannabis has anti-inflammatory and mild vasodilatation properties. At least some uses of some embodiments of the present invention are to deliver cannabis to promote these beneficial effects in the skin. For example, in one embodiment, inflammation is reduced on an area of human skin. In another embodiment, blood flow is increased. In yet another embodiment, the body area feels relaxed and less tensed after a few minutes of applying it to the specific area. Applying the remedy over the skin causes little to no side effects to the body, making it healthier than over the counters drugs, prescription drugs, and inhaling the cannabis in a form of a cigarette and effective. Nearly anyone can use the remedy from adults to children and babies. Individuals with arthritis, athletes, and people with chronic pain may particularly benefit from this remedy. The remedy may be used in a multiplicity of suitable places including, without limitation, doctors' offices, hospitals, clinics, convalescent homes, physical therapy centers, massage facilities, homes, etc.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Having fully described at least one embodiment of the present invention, other equivalent or alternative methods of providing cannabis-based remedies according to the present invention will be apparent to those skilled in the art. The invention has been described above by way of illustration, and the specific embodiments disclosed are not intended to limit the invention to the particular forms disclosed. For example, the particular implementation of the remedy may vary depending upon the particular type of delivery medium used. The mediums described in the foregoing were directed to liquid implementations; however, similar techniques are to implement the cannabis and alcohol mixture into various different mediums including, without limitation, lotions, gels, creams, ointments, rub-on solids, patches, etc. Non-liquid implementations of the present invention are contemplated as within the scope of the present invention. The invention is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. A method for treating arthritis in a human in need thereof consisting essentially of topically applying to the skin of the human in need thereof therapeutically effective amounts of a liquid mixture of ethanol, isopropyl, at least 30% of a cannabis leaf or a cannabis stem in the total method and a component selected from the group consisting of aloe, water and menthol.

* * * * *